United States Patent
Stankowski (10) Patent No.: US 12,241,050 B2
(45) Date of Patent: Mar. 4, 2025

(54) PERFUSION FILTER ASSEMBLY FOR INCREASED CROSS FLOW

(71) Applicant: Global Life Sciences Solutions USA LLC, Marlborough, MA (US)

(72) Inventor: Ralph Stankowski, Westborough, MA (US)

(73) Assignee: Global Life Sciences Solutions USA, LLC, Marlborough, MA (US)

( * ) Notice: Subject to any disclaimer, the term of this patent is extended or adjusted under 35 U.S.C. 154(b) by 371 days.

(21) Appl. No.: 17/464,599

(22) Filed: Sep. 1, 2021

(65) Prior Publication Data

US 2023/0066761 A1 Mar. 2, 2023

(51) Int. Cl.
*C12M 1/00* (2006.01)
*C12M 1/12* (2006.01)
*C12M 3/00* (2006.01)

(52) U.S. Cl.
CPC ............ *C12M 23/14* (2013.01); *C12M 23/26* (2013.01); *C12M 23/48* (2013.01); *C12M 25/02* (2013.01); *C12M 37/04* (2013.01)

(58) Field of Classification Search
CPC ...... C12M 23/14; C12M 23/26; C12M 23/48; C12M 25/02; C12M 37/04; C12M 29/04; B01D 2313/04; B01D 2313/06; B01D 63/087

See application file for complete search history.

(56) References Cited

U.S. PATENT DOCUMENTS

| | | | |
|---|---|---|---|
| 4,948,728 | A | 8/1990 | Stephanopoulos et al. |
| 5,139,946 | A | 8/1992 | Howell et al. |
| 5,714,384 | A | 2/1998 | Wilson et al. |
| 6,368,592 | B1 | 4/2002 | Colton et al. |
| 8,580,560 | B1 | 11/2013 | Ellis et al. |
| 9,017,997 | B2 | 4/2015 | Wuenn et al. |
| 10,464,064 | B1 | 11/2019 | Wikswo et al. |
| 10,532,324 | B1 | 1/2020 | Masquelier et al. |
| 10,752,874 | B2 | 8/2020 | Johnson et al. |
| 10,988,723 | B1 | 4/2021 | Hatch et al. |
| 11,027,239 | B2 | 6/2021 | Zhang et al. |
| 2004/0029266 | A1 | 2/2004 | Barbera-Guillem |
| 2005/0280179 | A1 * | 12/2005 | Stankowski ........... B01D 63/08 264/275 |

(Continued)

FOREIGN PATENT DOCUMENTS

| EP | 0817834 A1 | 1/1998 |
|---|---|---|
| EP | 3356509 B1 | 7/2019 |

(Continued)

OTHER PUBLICATIONS

Search Report received in International Application No. PCT/EP2022/073787 dated Dec. 21, 2022, 4 pages.

(Continued)

*Primary Examiner* — William H. Beisner
*Assistant Examiner* — Danielle B Henkel
(74) *Attorney, Agent, or Firm* — Jeff B. Vockrodt; CM Law (57) ABSTRACT

Filter holders and membranes are provided that can be included within a bioreactor bag system. The filter holders and membranes include features that abut the bottom of the filter membrane and prevent or reduce sagging of the porous filter region during use.

14 Claims, 7 Drawing Sheets

(56) References Cited

U.S. PATENT DOCUMENTS

| | | |
|---|---|---|
| 2006/0263873 A1 | 11/2006 | Levine et al. |
| 2010/0221838 A1* | 9/2010 | Burgess ............... B01D 63/087 |
| | | 422/68.1 |
| 2011/0212493 A1 | 9/2011 | Hirschel et al. |
| 2011/0250585 A1 | 10/2011 | Ingber et al. |
| 2013/0196375 A1 | 8/2013 | Strobbe |
| 2014/0178992 A1 | 6/2014 | Nakashima et al. |
| 2015/0004686 A1 | 1/2015 | Goral et al. |
| 2018/0326417 A1 | 11/2018 | Wikswo et al. |
| 2018/0346864 A1* | 12/2018 | Faldt ....................... C12M 23/14 |
| 2019/0105609 A1* | 4/2019 | Zhang ................. A61M 1/3482 |
| 2019/0134568 A1 | 5/2019 | Roy |
| 2019/0330579 A1 | 10/2019 | Guenat et al. |
| 2019/0336971 A1 | 11/2019 | Wikswo et al. |
| 2020/0071657 A1 | 3/2020 | Johnson et al. |
| 2020/0181555 A1 | 6/2020 | Hinojosa et al. |
| 2020/0231921 A1 | 7/2020 | Zhang et al. |
| 2020/0354668 A1 | 11/2020 | Sawyer et al. |
| 2021/0069648 A1 | 3/2021 | Bransby et al. |
| 2021/0205810 A1 | 7/2021 | Haun et al. |
| 2021/0308628 A1 | 10/2021 | Hennessy et al. |
| 2021/0308634 A1 | 10/2021 | Hennessy et al. |
| 2022/0111338 A1 | 4/2022 | Stankowski et al. |
| 2022/0213420 A1* | 7/2022 | Parziale ................. C12M 29/20 |
| 2022/0314174 A1 | 10/2022 | Albagli et al. |
| 2023/0272321 A1 | 8/2023 | Maoz et al. |
| 2024/0002898 A1 | 1/2024 | Doryab et al. |

FOREIGN PATENT DOCUMENTS

| | | |
|---|---|---|
| KR | 20060019241 A | 3/2006 |
| WO | 0141905 A1 | 6/2001 |
| WO | 2012158108 A1 | 11/2012 |
| WO | 2015034416 A1 | 3/2015 |

OTHER PUBLICATIONS

Search Report received in International Application No. PCT/EP2022/073789 dated Dec. 21, 2022, 4 pages.

Written Opinion received in International Application No. PCT/EP2022/073787 dated Dec. 21, 2022, 18 pages.

Written Opinion received in International Application No. PCT/EP2022/073789 dated Dec. 21, 2022, 18 pages.

* cited by examiner

PERFUSION FILTER ASSEMBLY FOR INCREASED CROSS FLOW

BACKGROUND OF THE INVENTION

The bio-processing industry has traditionally used stainless steel systems and piping in manufacturing processes for fermentation and cell cultivation. These devices are designed to be steam sterilized and reused. Cleaning and sterilization are however costly labor-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last ten years—that of using plastic, single-use disposable bags and tubing, to replace the usual stainless steel tanks.

In particular bioreactors, traditionally made of stainless steel, have been replaced in many applications by disposable bags which are rocked to provide the necessary aeration and mixing necessary for cell culture. These single-use bags are typically provided as sterile units and eliminate the costly and time-consuming steps of cleaning and resterilization. The bags are designed to maintain a sterile environment during operation thereby minimizing the risk of contamination.

One of the successful disposable bioreactor systems uses a rocking table on which a bioreactor bag is placed. The bioreactor bag is partially filled with liquid nutrient media and the desired cells. The table rocks the bag providing constant movement of the cells in the bag and also efficient gas exchange from the turbulent air liquid surface. The bag, typically, has at least one gas supply tube for the introduction of air, carbon dioxide, nitrogen or oxygen, and at least one exhaust gas tube to allow for the removal of respired gases. Nutrients can be added through other tubes.

During cultivation, the cells produce waste e.g. metabolites, ammonium ions and lactate, which have an inhibitory effect on cells. This effect becomes an issue particularly in cultivation at high cell densities, which are required for cost-effective production of biopharmaceuticals such as therapeutic proteins or virus antigens. One way to reduce the concentrations of inhibitory metabolites is to use perfusion cultivation where culture medium is bled off by hydraulic flow through a filter which retains the cells but lets the metabolites and proteins pass through the filter. Expressed proteins can then be recovered from the filtrate and fresh culture medium is continuously supplied to the bioreactor to compensate for the lost liquid. Perfusion filters can typically be installed in the interior of a bioreactor (or outside).

Perfusion filters may be incorporated into a bioreactor bag in several ways. One way to provide a perfusion filter to a disposable bioreactor is to provide the perfusion filter to a device comprising a screen and having a connector for attaching a tube for retrieving filtrate, often waste, and just let the device with a filter and screen float within the bioreactor. Another way to provide a perfusion filter has been described in U.S. Pat. No. 9,017,997. Here it is described that the perfusion filter is attached to the bottom of the bioreactor bag. WO2012/158108 and WO2015/034416 describe flexible bags for cell culture provided with internal filters attached to the wall of the bag by a filter holding device, adapted to maintain a distance between the filter and the wall of the bag.

Figure 1A:
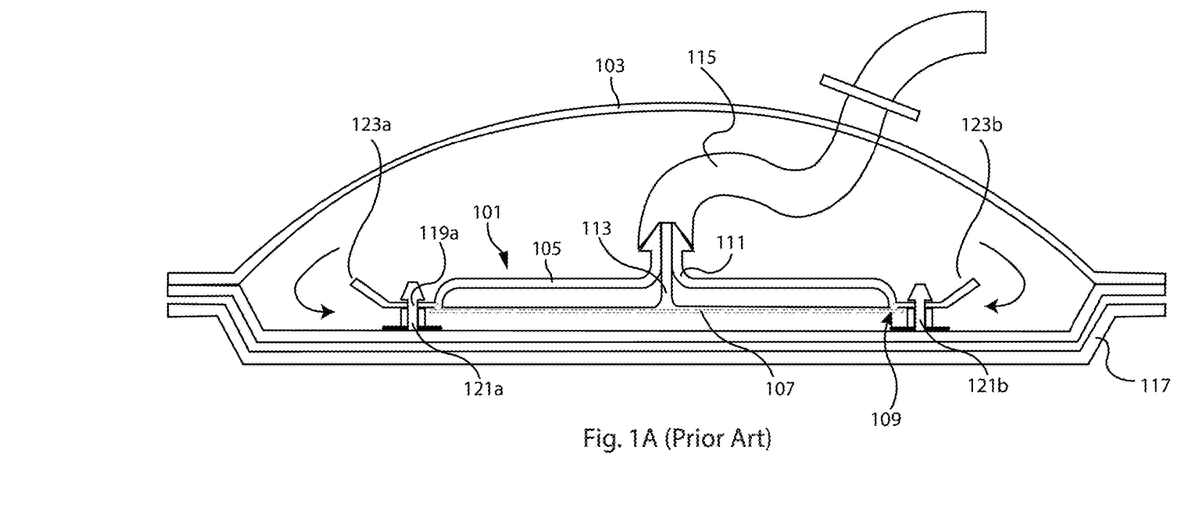
FIG. 1A shows a prior art perfusion filter assembly.

EP 3 356 509 B1 describes a filter holding device that can be used within a bioreactor bag. FIG. 1A shows schematically a cross section side view of the filter holding device 101. The filter holding device 101 is provided in a flexible bag 103. The filter holding device 101 is suitably a flat or somewhat curved plate. The filter holding device 101 comprises some kind of distancing means on one side of a middle part 105 of the filter holding device. This distancing means could be for example ribs or a screen or some other kind of structure. The distancing means is provided on the side of the filter holding device to which a filter 107 should be attached. In this description the word filter is used but it could also be a membrane or a bioprocessing separation device used to retain or refrain.

Figure 1B:
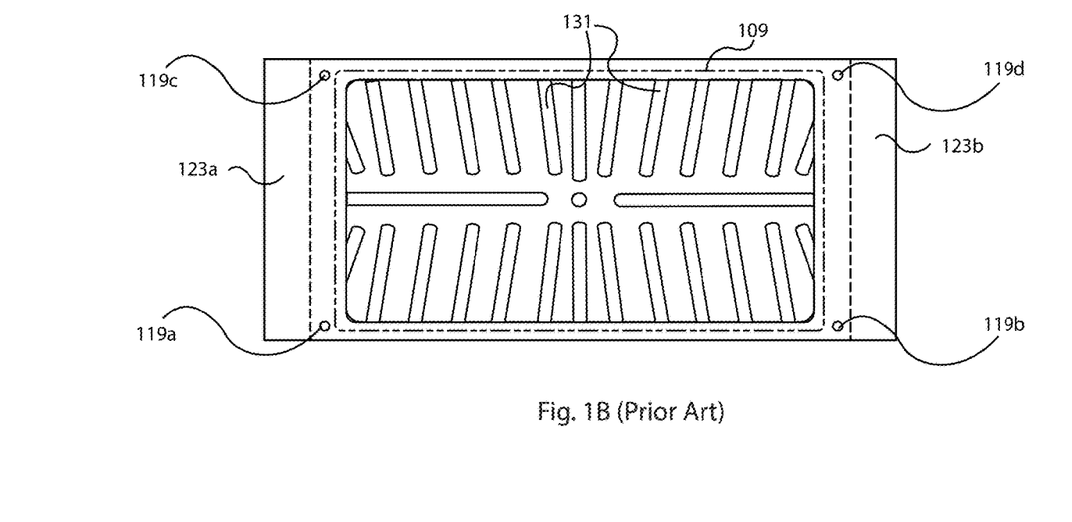
FIG. 1B shows a top down view of a portion of the prior art filter assembly shown in FIG. 1A.

A distancing means in the form of ribs are further shown and described in relation to FIG. 1B, which shows a schematic bottom view of the filter holding device shown in FIG. 1A. In this view the filter sealing area 109 can be seen to enclose the distancing means, here in the form of ribs 131. All the ribs are given the same numbers. The configuration and number of the ribs could vary. The function of the ribs is to hold the filter and distance the filter from the other side of the filter holding device such that the fluid can be filtered through the filter and drawn out through the opening 113 and port 111.

The filter holding device 101 comprises further a filter sealing area 109 provided around the distancing means. The filter sealing area 109 is arranged to be sealed to a periphery of the filter 107 to be held by the filter holding device. The filter will then be covering the distancing means when it has been sealed to the filter sealing area 109 of the filter holding device. In one embodiment the filter can also be sealed to one or more areas of the distancing means in order to prevent the filter from slacking. Furthermore, the filter holding device comprises a port 111 arranged around an opening 113 in the filter holding device 101, which opening connects fluidically with the spaces between the ribs. Said port 111 is arranged to be connected to a tube 115 for retrieving filtrate, usually waste. The port 111 and opening 113 are in one embodiment of the invention provided in the middle of the filter holding device 101 and centered inside the filter sealing area 109. However, the port and opening can also be provided in another position but they still need to be provided within the filter sealing area 109.

The flexible bag is shown here placed in a rocker tray 117. Attaching means are provided to the filter holding device for attaching the filter holding device to an inner surface of the flexible bag such that the at least one filter held by the filter holding device is provided at a distance from the inner surface of the flexible bag. In this embodiment of the invention the attaching means are provided as four openings 119a-d (only 119a and 119b can be seen) in the filter holding device and four stand-offs 121a-d to be received in the openings. Each one of the stand-offs 121a-d is attached one to each opening 119a-d in the filter holding device in a suitable way for example by heat sealing or my mechanical retention. The stand-offs 121a-d are then attached to the flexible bag inner surface for example by heat sealing or mechanical retention. In this embodiment the stand-offs 121a-d are shown to be attached to the bottom wall of the flexible bag 103 but they could as well be attached to another wall. Another possibility would also be that the stand-offs are molded together with the filter holding device. The number of openings and stand-offs and their positions could be varied. The height of the attaching means which in this shown embodiment are the standoffs, should be adapted for assuring that there will be a suitable distance between the filter and the bag inner surface for letting fluid flow between the filter and the bag surface and thereby create a crossflow effect over the filter, also called tangential flow. This tangential flow or crossflow over the filter will prevent fouling and clogging and will increase the life time of the filter. In another embodiment the attaching means is in the form of sealing two opposite sides of the filter holding device to the inner surface of the flexible bag. In order to provide a passage or channel for the fluid to pass between the filter and the bag surface the filter holding device needs to be bent or curved in some way.

The filter holding device 101 further comprises two deflector areas 123*a*, 123*b*. These deflector areas 123*a*, 123*b* are provided on opposite sides of the filter holding device and outside the filter sealing area 109. The deflector areas 123*a*, 123*b* are angled in relation to the rest of the filter holding device and they are pointing away from the inner surface of the flexible bag to which the filter holding device is attached when the filter holding device is mounted to the flexible bag. The deflector areas 123*a*, 123*b* affects the fluid flow in the flexible bag. The rocking tray is moved in a specific pattern such that the fluid inside the flexible bag is moving back and forth in a wave like motion. The deflector areas 123*a*, 123*b* will direct and force more fluid to pass between the filter and the bag surface to which the filter holding device is attached. Thereby a crossflow effect over the filter is created which will reduce clogging and fouling.

The present inventors have perceived a need to improve on filter membranes and filter holding assemblies in order to incorporate membrane filters made by more advanced membrane production techniques that incorporate materials having different characteristics than the typical materials utilized in filter holders used within bioreactor bags. Accordingly, the present invention seeks to improve microporous membranes and filter assemblies for holding those membranes.

SUMMARY OF THE INVENTION

In one aspect, the invention involves a filter assembly comprising: a support plate; a filter membrane comprising a porous filter region, wherein the filter membrane is bonded to the support plate in a peripheral region of the filter membrane; and at least one support structure abutting the bottom of the filter membrane adapted to prevent or reduce sagging of the porous filter region during use. The support structure may be a post with a support head, and the post connects to the support plate through an opening in the filter membrane within the porous region of the filter membrane. The support structure may be a frame comprising at least one cross-member under the porous region and at least one opening under the porous region.

In another aspect, the invention involves a bioreactor bag comprising: a flexible bag having an inner surface and an outer surface; a filter assembly, the filter assembly comprising: a support plate; a filter membrane comprising a porous filter region, wherein the filter membrane is bonded to the support plate in a peripheral region of the filter membrane; and at least one support structure abutting the bottom of the filter membrane adapted to prevent or reduce sagging of the porous filter region during use; wherein the filter assembly is mounted in the flexible bag with an exposed surface of the porous filter region facing the bottom of the flexible bag.

In another aspect, the invention involves a filter membrane includes support regions surrounding the opening in the filter membrane within the porous region of the filter membrane, the support regions lacking pores.

DETAILED DESCRIPTION OF THE INVENTION

The present invention involves perfusion filter assemblies and filer membranes for use in those perfusion filter assemblies. The perfusion filter assemblies and perfusion membranes disclosed herein are particularly adapted to membranes that are made with advanced processes, such as photolithography and etching. The present inventors have found that membranes made according to these processes have material characteristics that make them unsuitable for use with traditional perfusion filter assemblies. For example, polyimide membranes can be difficult to bond to the polyethylene components used in perfusion filter assemblies, including perfusion filter bags. The filter membranes and filter assemblies disclosed herein include features that overcome one or more of these obstacles.

Figure 2:
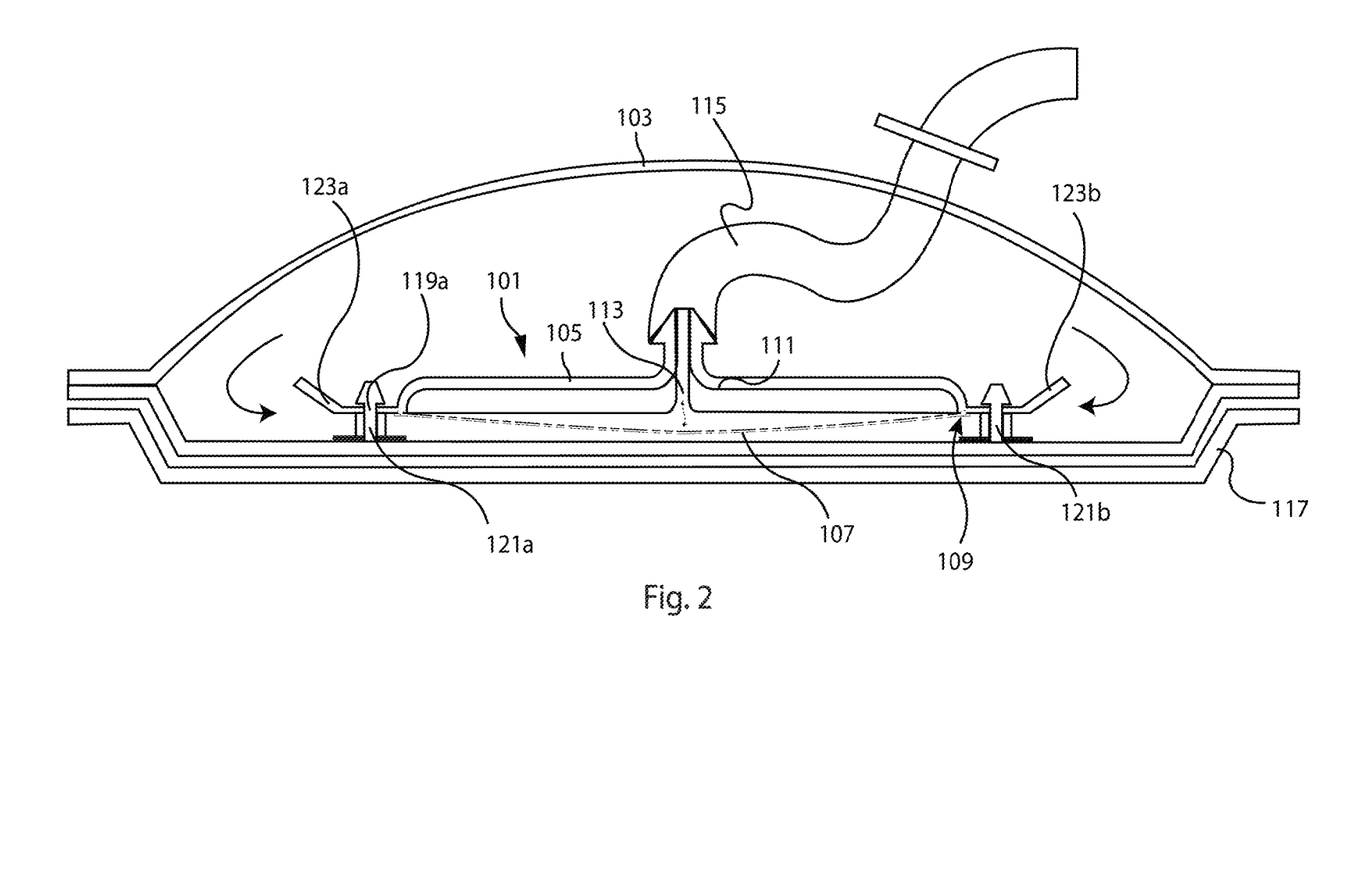
FIG. 2 shows a filter assembly where sagging of the filter membrane is occurring.

The present inventors have observed that the filter membrane 107 may sag as shown in FIG. 2 under certain conditions. The sagging of the filter membrane 107 may result in undesirable flow blockage when the filter membrane 107 is placed near the bottom of a bioreactor bag 103 as shown in FIG. 2. This problem may be exacerbated when the bioreactor bag is used with a rocking motion.

In one aspect, the present invention involves the use of a support structure comprising a support pin having a portion abutting the bottom of the filter membrane adapted to prevent or reduce sagging of the porous filter region during use.

Figure 3A:
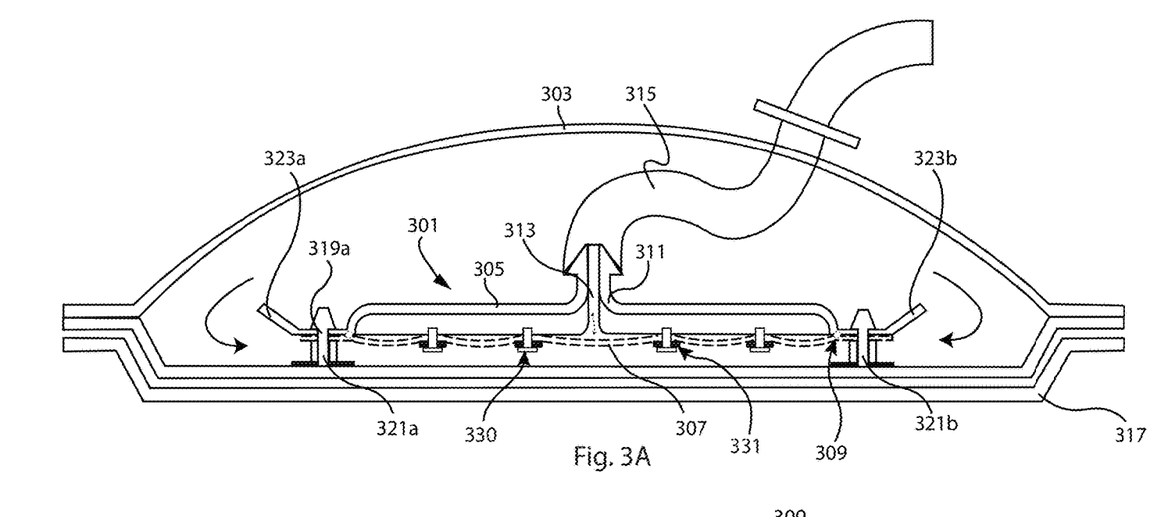
FIG. 3A shows a perfusion filter membrane utilizing membrane support holes according to an embodiment of the invention.
Figure 3B:
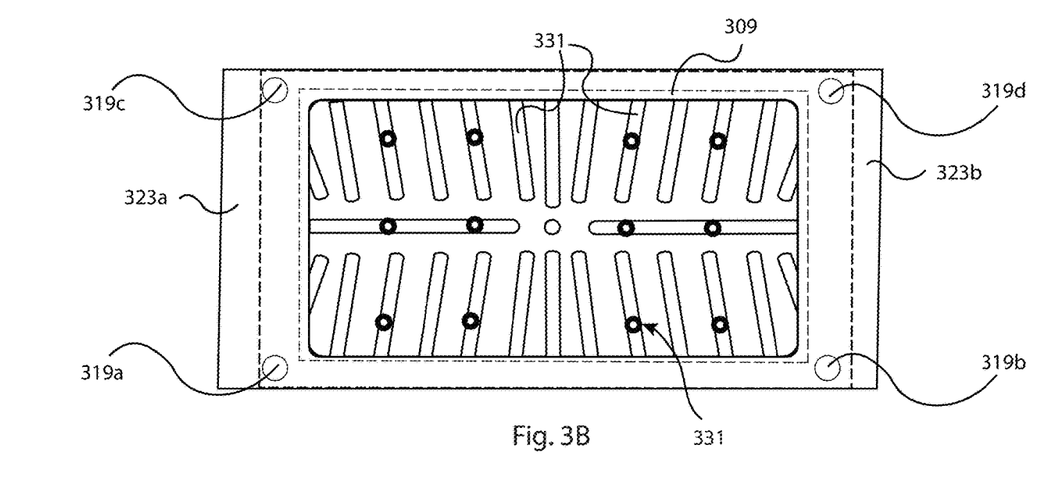
FIG. 3B shows top down view of the perfusion filter membrane utilizing membrane support holes shown in FIG. 3A.

As shown in FIGS. 3A-B, a bioreactor bag 303 includes a filter holding device 301 placed at the bottom of the bioreactor bag 303 where the filter membrane 307 faces the bottom of the bioreactor bag 303. A port 311 allows filtered fluid to exit the bioreactor bag through opening 313 and out of the tube 315. The filter holding device includes openings 319*a-d* which are used for attaching to standoffs 321*a-d* (only 321*a* and 321*b* are shown). The filter holding device 301 includes deflector areas 323 that improve the flow under the filter holding device 301 within the bioreactor bag 305. The bioreactor bag 305 may be placed on a rocker tray 317.

The filter holding device 301 may be attached to the bottom of the bioreactor bag 303 using standoffs 321a-d (only 321a and 321b are shown) which correspond to holes 319a-d as seen in FIG. 3B.

The filter membrane 307 may be attached to the filter holding device 301 using a bond 309. The bond 309 can be a heat weld in the case that the filter membrane is made of a material that can be heat bonded to the filter holding device 301. For example, where both filter membrane 307 and filter holding device 301 are made from polyethylene, the bond 309 may be a heat weld. The bond 309 must be sufficient to prevent liquid from leaking from the bioreactor bag past the filter membrane 307.

The support structure may include support pins 330 that attach directly to the middle part 305 of the support structure. The support pins 330 include several configurations but so long as a portion of the support pin, such as a head abuts a portion of the filter membrane 307 and reduces sagging in particular areas. The support pins 330 may be threaded such that they may be screwed into the middle part 305 of the filter membrane support. The support pins are provided with seals 331, which may be O-rings. The O-ring is typically made from a resilient material such as rubber, which provides compression and sealing around the support post 330 and prevent leakage around the filter membrane 309.

In another aspect, the present invention involves the use of a support structure comprising a frame having a portion abutting the bottom of the filter membrane adapted to prevent or reduce sagging of the porous filter region during use.

Figure 4A:
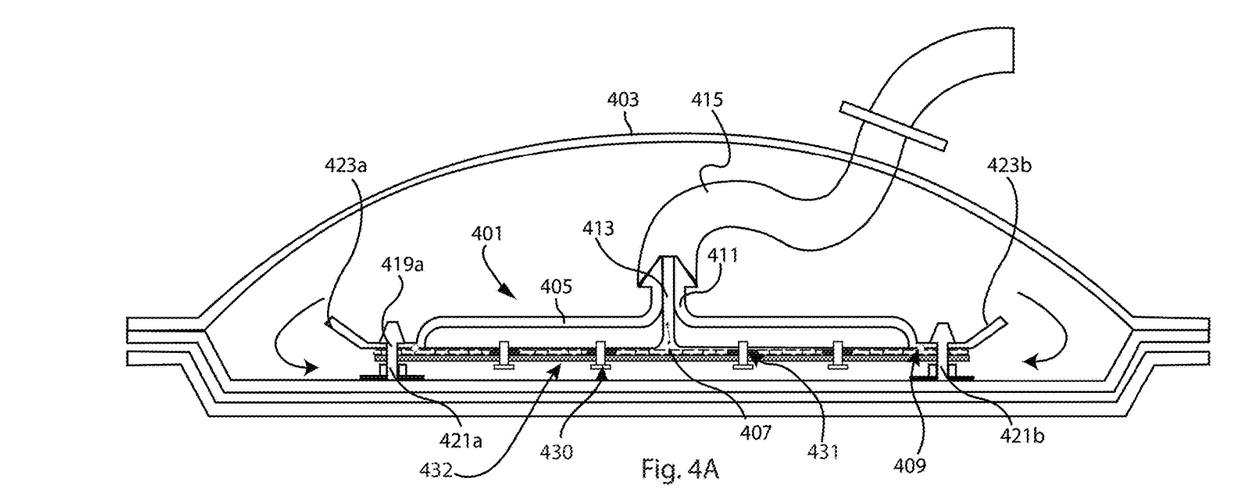
FIG. 4A shows a perfusion filter assembly utilizing a support frame according to an embodiment of the invention.
Figure 4B:
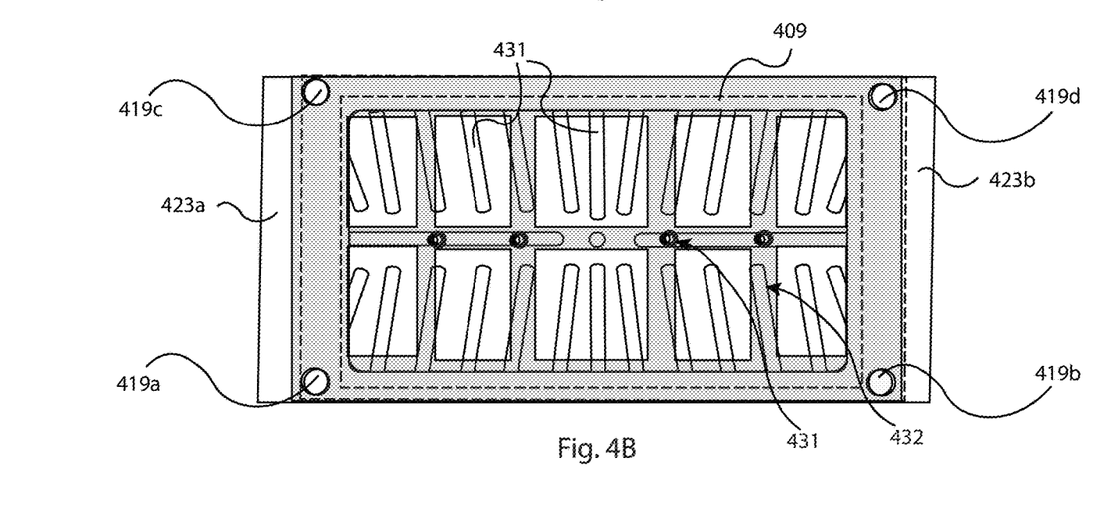
FIG. 4B shows bottom up view of the perfusion filter membrane shown in FIG. 4A.

As shown in FIGS. 4A-D, a bioreactor bag 403 includes a filter holding device 401 placed at the bottom of the bioreactor bag 403 where the filter membrane 407 faces the bottom of the bioreactor bag 403. A port 411 allows filtered fluid to exit the bioreactor bag through opening 413 and out of the tube 415. The filter holding device includes openings 419a-d which are used for attaching to standoffs 421a-d (only 421a and 421b are shown). The filter holding device 401 includes deflector areas 423 that improve the flow under the filter holding device 401 within the bioreactor bag 405. The bioreactor bag 405 may be placed on a rocker tray 417. The filter holding device 401 may be attached to the bottom of the bioreactor bag 403 using standoffs 421a-d (only 421a and 421b are shown) which correspond to holes 419a-d as seen in FIG. 4B.

The filter membrane 407 may be attached to the filter holding device 401 using a bond 409. The bond 409 can be a heat weld in the case that the filter membrane is made of a material that can be heat bonded to the filter holding device 401. For example, where both filter membrane 407 and filter holding device 401 are made from polyethylene, the bond 409 may be a heat weld. The bond 409 must be sufficient to prevent liquid from leaking from the bioreactor bag past the filter membrane 407.

Figure 4C:
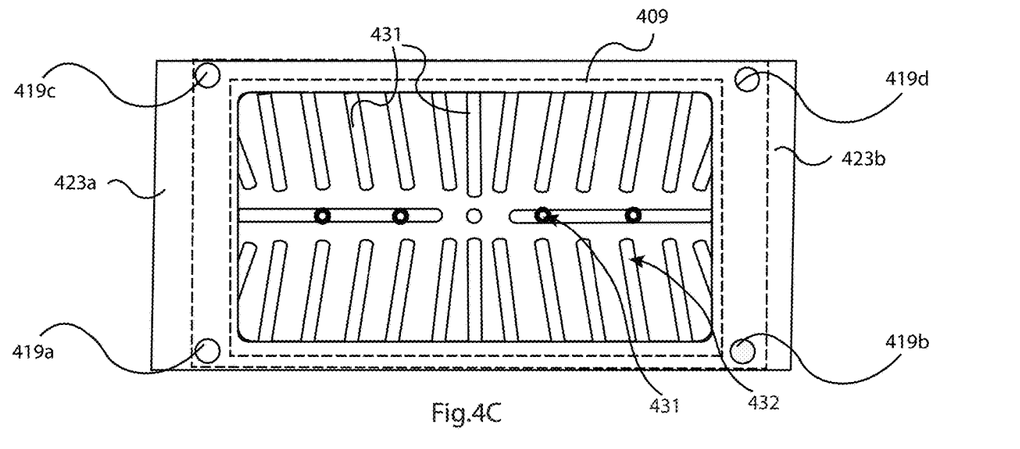
FIG. 4C shows a bottom up view of the support plate of the perfusion filter membrane shown in FIG. 4A.
Figure 4D:
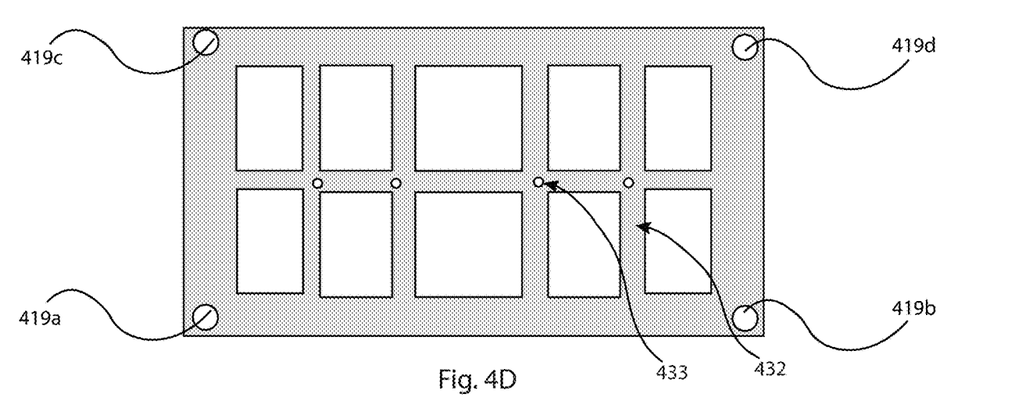
FIG. 4D shows a bottom up view of the support frame of the perfusion filter membrane shown in FIG. 4A.

The support structure may include a frame 432 that attach directly to the middle part 405 of the support structure. In the case where a frame 342 is used, the bond 409 may be an O-ring that is placed between the frame 342 and the filter support 405. The support pins 430 may be threaded such that they may be screwed into the middle part 405 of the filter membrane support. The support pins are provided with seals 431, which may be O-rings. The O-ring is typically made from a resilient material such as rubber, which provides compression and sealing around the support post 430 and prevent leakage around the filter membrane 409. Where a frame 432 is used, the support pin 330 head abuts the support frame 432 which abuts the filter membrane 407 and prevents sagging. FIGS. 4C-D show the deconstructed filter holding device and frame 432.

Figure 5A:
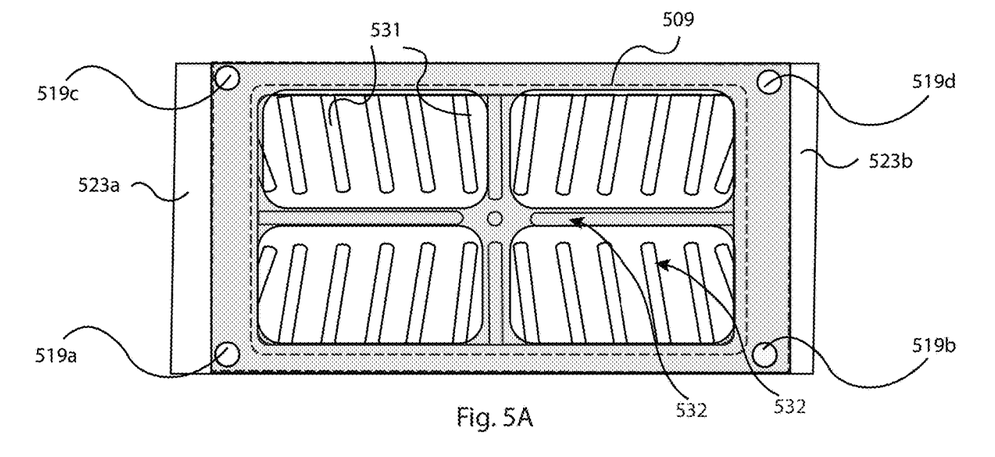
FIG. 5A shows a bottom up view of a support plate and frame according to another embodiment of the invention.
Figure 5B:
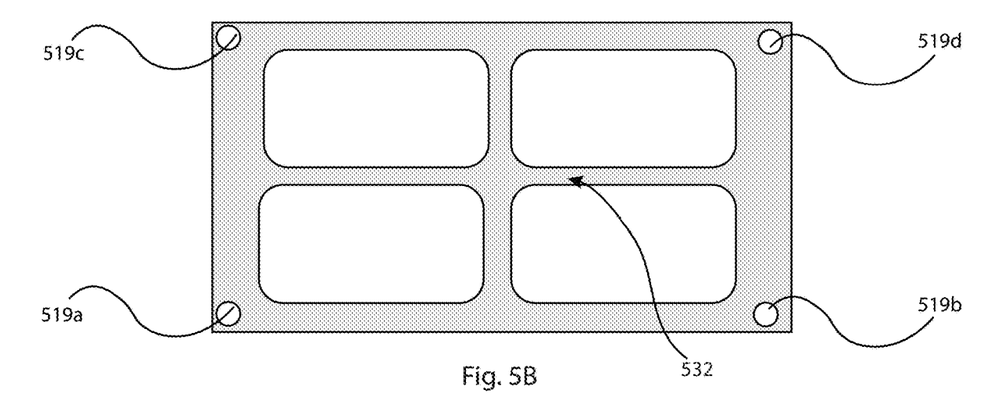
FIG. 5B shows a bottom up view of the frame shown in FIG. 5A.

FIGS. 5A-B show an alternative embodiment of a frame 532 that can be used without support pins. In this case, the support frame 532 does not include support pins and eliminates the need for seals since the filter membrane is a unitary part. The frame includes holes 519a-c adapted to interface with standoffs for supporting the filter membrane holder. The filter holder includes ribs 531 that abut portions of the filter membrane. The frame may be used with a filter membrane that can be attached to the filter membrane support using a bond 509 or alternatively an O-ring placed between the filter membrane and either the frame 532 and membrane or the filter holder and the membrane.

Figure 6A:
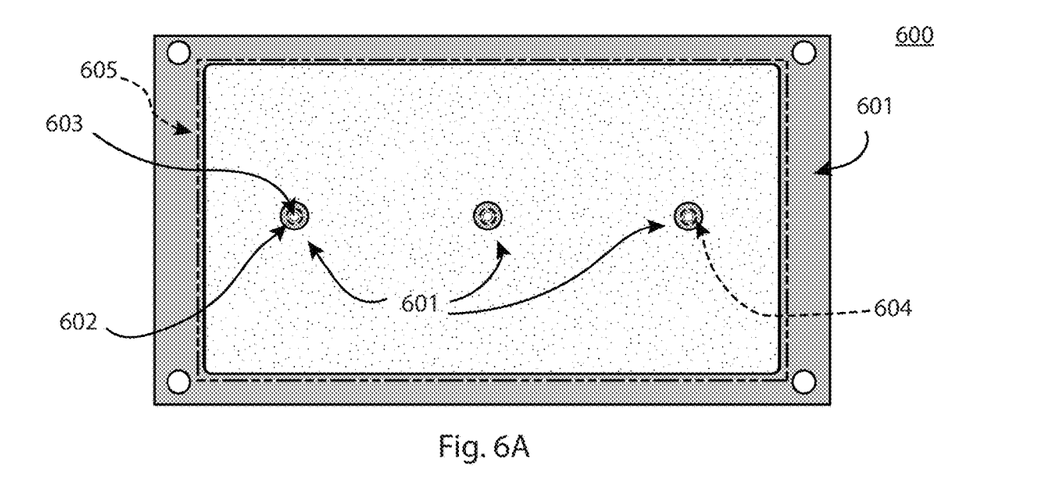
FIG. 6A shows a first perfusion filter membrane according to an embodiment of the invention.
Figure 6B:
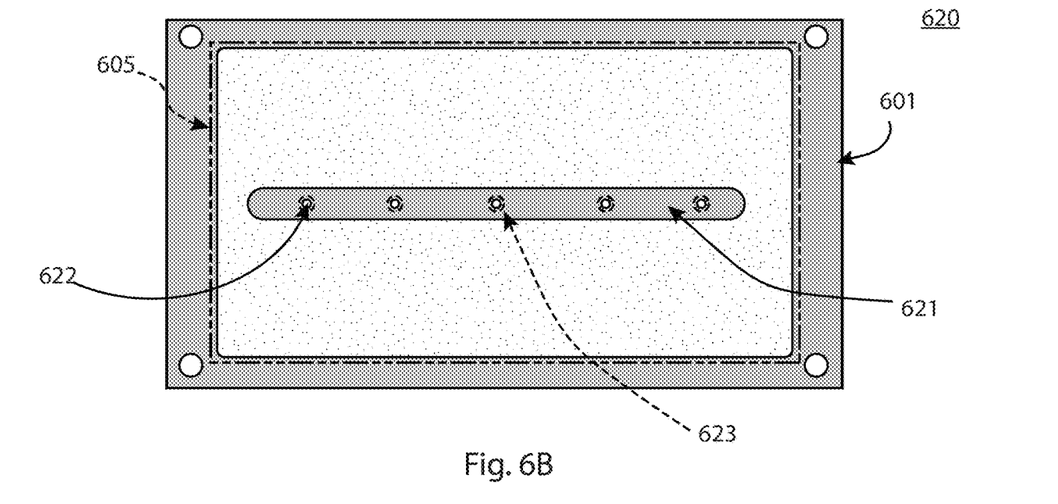
FIG. 6B shows a second perfusion filter membrane according to an embodiment of the invention.

FIGS. 6A-6B show filter membranes that can be used with certain embodiments of this invention. The filter membrane 600 includes three holes 603 that are adapted to allow a support pin to be placed in the membrane 600. Each of the support holes is surrounded by a support region 602 that lacks pores. The support region 602 is useful for interfacing with an O-ring 604 indicated by dashed lines since they are not part of the filter membrane. The dashed line 605 may represent a heat bond region or the placement of an O-ring in the case that a frame is used. FIG. 6B shows an alternative embodiment where a support region 621 surrounds several holes 622, which each can use their own O-ring 623.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims

What is claimed is:

1. A bioreactor bag comprising:
    a flexible bag having an inner surface and an outer surface;
    a perfusion filter assembly, the filter assembly comprising:
        a horizontally oriented support plate with an opening proximate the top that is adapted to be connected with a tube for retrieving filtrate;
        a filter membrane comprising a porous filter region, wherein the filter membrane is bonded proximate the bottom of the support plate in a peripheral region of the filter membrane; and
        at least one support structure abutting the bottom of the filter membrane adapted to prevent or reduce sagging of the porous filter region during use;
    wherein the filter assembly is mounted in the flexible bag with an exposed surface of the porous filter region facing the bottom of the flexible bag and a plurality of stand-offs contact the inner surface of the bag and filter assembly that are adapted to assure that there is a distance between the filter assembly and the inner surface of the flexible bag for fluid flow between the filter membrane and the inner surface of the flexible bag.

2. The bioreactor bag of claim 1, wherein the support structure is post with a support head, and the post connects to the support plate through an opening in the filter membrane within the porous region of the filter membrane.

3. The bioreactor bag of claim 2, wherein the filter assembly comprises a plurality of posts.

4. The bioreactor bag of claim 3, wherein the posts are arranged into rows.

5. The bioreactor bag of claim 2, wherein a seal is provided, the seal being configured to prevent leakage of liquid around the porous filter region in the region of the support structure.

6. The bioreactor bag of claim 5, wherein the seal is an O-ring.

7. The bioreactor bag of claim 1, wherein the support structure is a frame comprising at least one cross-member under the porous region and at least one opening under the porous region.

8. The bioreactor bag of claim 7, wherein the frame includes two or more openings under the porous region.

9. The bioreactor bag of claim 7, wherein the frame includes four or more openings under the porous region, and the four or more openings are organized in a grid pattern.

10. The bioreactor bag of claim 7, wherein the filter membrane includes support regions surrounding the opening in the filter membrane within the porous region of the filter membrane, the support regions lacking pores.

11. A bioreactor bag comprising:
    a flexible bag having an inner surface and an outer surface;
    a perfusion filter assembly, the filter assembly comprising:
        a horizontally oriented support plate with an opening proximate the top that is adapted to be connected with a tube for retrieving filtrate;
        a filter membrane comprising a porous filter region; and
        at least one support frame abutting the bottom of the filter membrane adapted to prevent or reduce sagging of the porous filter region during use, the at least one support frame comprising at least one cross-member under the porous filter region;
    wherein the filter assembly is mounted in the flexible bag with an exposed surface of the porous filter region facing the bottom of the flexible bag and a plurality of stand-offs contact the inner surface of the bag and filter assembly that are adapted to assure that there is a distance between the filter assembly and the inner surface of the flexible bag for fluid flow between the filter membrane and the inner surface of the flexible bag.

12. The bioreactor bag of claim 11, wherein the frame includes two or more openings under the porous region.

13. The bioreactor bag of claim 11, wherein the frame includes four or more openings under the porous region, and the four or more openings are organized in a grid pattern.

14. The bioreactor bag of claim 11, wherein the filter membrane includes support regions surrounding the opening in the filter membrane within the porous region of the filter membrane, the support regions lacking pores.

* * * * *